United States Patent [19]

Kankare et al.

[11] Patent Number: 5,308,754

[45] Date of Patent: May 3, 1994

[54] ELECTROGENERATED LUMINESCENCE IN SOLUTION

[76] Inventors: Jouko J. Kankare, Paljaspää 8 E 3, SF-20610 Turku 61; Haapakka, Keijo E., Turku, both of Finland

[21] Appl. No.: 780,364

[22] Filed: Oct. 22, 1991

Related U.S. Application Data

[63] Continuation-in-part of Ser. No. 323,768, Mar. 15, 1989, abandoned.

[30] Foreign Application Priority Data

Mar. 21, 1988 [SE]  Sweden .............................. 8801011-1

[51] Int. Cl.⁵ ...................... C12Q 1/00; G01N 21/76; G01N 33/553
[52] U.S. Cl. ..................................... 435/7.4; 436/518; 436/525; 436/172; 436/805; 436/806; 435/968; 435/7.1
[58] Field of Search .................. 435/5, 6, 7.2, 7.4, 435/968, 7.1; 436/518, 525, 172, 805, 806, 816

[56] References Cited

U.S. PATENT DOCUMENTS

| 4,280,815 | 7/1981 | Oberhardt et al. | 422/55 |
| 4,374,120 | 2/1983 | Soini et al. | 436/546 |
| 4,857,475 | 8/1989 | Dakubu | 436/546 |
| 4,962,045 | 10/1990 | Picozza et al. | 436/56 |

FOREIGN PATENT DOCUMENTS 8602734  5/1986  PCT Int'l Appl. .

OTHER PUBLICATIONS

Diamandis et al. (Nov. 15, 1990) Anal. Chem. 62(22): 1149A-1157A.

Primary Examiner—Charles L. Patterson, Jr.
Attorney, Agent, or Firm—Bucknam & Archer

[57] ABSTRACT

A method whereby the presence and/or amount of a chemical moiety containing terbium is determined by applying an electrical pulse to an electrode immersed in a solution and measuring the delayed light emission after some time from the end of the pulse, said chemical moiety being either bound to said electrode and/or present in said solution and said emitted light being taken as an indication of the amount of the chemical moiety present in the proximity of said electrode.

4 Claims, 3 Drawing Sheets

ELECTROGENERATED LUMINESCENCE IN SOLUTION

This application is a continuation-in-part of U.S. Ser. No. 323,768 filed Mar. 15, 1989, now abandoned.

FIELD OF INVENTION

This invention relates to a method according to which a luminescent compound in aqueous or non-aqueous solution is excited by an electrical pulse either directly by electron transfer from an electrode or indirectly by some mediating electrochemically induced reaction. The light emission from the compound is detected after the end of the excitation pulse.

The new method may find applications in those fields where a very low detection limit is required, e.g. in analytical methods based on binding assays such as immunoassays and nucleic acid hybridization assays.

The analytical methods based on luminescence in its various modifications are generally known for their sensitivity, but they have their shortcomings at very low concentrations of the emitting species. The sensitivity of fluorescence is limited by Rayleigh and Raman scattering phenomena as well as fluorescent impurities which increase the nonspecific background emission.

Phosphorescence is mainly restricted to solid state and the emission of those very few compounds which have room temperature phosphorescence in solution is generally extremely sensitive to oxygen, which interferes with their practical applications. The delayed fluorescence of some lanthanide chelates which allows a very low detection limit has been used as a basis of an immunoassay method. The methods based on the conventional fluorescence and phosphorescence use excitation by light and need appropriate light source and optics. The methods based on chemiluminescence (CL) do not need excitation optics and the instrumentation is generally very simple. However, the CL methods are often subject to serious chemical interference.

The method described in this invention avoids certain shortcomings of other luminescence methods. No excitation optics are needed and the electronic instrumentation required for the pulse excitation by electric current can be made very simple. The crux of the invention resides in the fact that the nonspecific background emission is totally eliminated by using appropriate luminescent compounds with long-lived luminescence and by measuring light emission after some time delay from the end of the excitation pulse.

DESCRIPTION OF THE PRIOR ART

Electrogenerated chemiluminescence (ECL) has been known for a long time. Its use in immunoassay has been proposed by Bard et al. (D. Ege, W. Becker and A. Bard, Anal. Chem. 56 (1984) 2413, PCT Int. Appl. WO 86/02734). They suggest to use ruthenium- or osmium-containing compounds as labels in binding assay. Platinum and glassy carbon are used as the material for the working electrode in the example given, and the light emission from the electrode is measured during the potential pulse.

As shown by the present authors, electrogenerated luminescence is generated at oxide-covered aluminum or tantalum electrodes by many inorganic ions (K. Haapakka et al., Anal. Chim. Acta 171 (1985) 259) and fluorescent organic compounds (K. Haapakka et al., Anal. Chim Acta 207 (1988) 195) in the presence of suitable oxidizing agents. In these studies the light emission from the electrode was measured also during the potential pulse applied the electrodes.

It would be very advantageous to have a method which allows inexpensive, preferentially disposable electrodes and makes use of compounds having long-lived luminescence which is relatively free of interferences. Such a method would find use e.g. in binding assays such as homogeneous and heterogeneous immunoassay allowing rather simple and inexpensive instrumentation. In the immunassay or more generally binding assay two components react specifically with each other and the product is quantitated by a suitable, highly sensitive method. If it is necessary to separate the product before its determination, the method is called heterogeneous, and homogeneous if no separation step is necessary. Because of a simpler procedure, homogeneous assays are preferable, but so far heterogeneous assays have provided lower detection limits. Typically in these methods the presence of a compound is indicated by labelling it with a chemical moiety which can be determined with a high sensitivity, e.g. radioactive isotope, enzyme, fluorescent compound, etc. Especially advantageous is labelling with a fluorescent compound which has a slow emissive decay of the excited state. Most of the samples subjected to immunoassay contain natural fluorescent species which increase the background emission and consequently impair the detection limit in the conventional fluorometric determination. Chelates of europium and terbium have the lifetime of their fluorescence emission in the millisecond region, i.e. several orders of magnitude longer than the "natural" fluorescence of organic compounds of biological origin.

Homogeneous assay based on luminescence is possible if the antibody-antigen complex adsorbed on the surface can be selectively excited without the excitation of labelled compound in the solution. This has been previously achieved (U.S. Pat. No. 3,939,350 (1976)) by using labelled antigens bound to antibodies linked to a quartz slide. The sample is excited from another side of the slide, with the beam totally reflecting from the slide surface. In the measurement only the solid-phase bound fraction is excited, thus obviating the separation step. The method places strict optical quality requirements on the sample slide and consequently its use in routine assays is restricted. Also the scattering and background fluorescence remain severe problems. Preferential excitation of luminescent compounds on the surface or its immediate vicinity can be technically more easily achieved by using electrogenerated luminescence and the influence of background fluorescence can be minimized by using labels with delayed electroluminescence.

DETAILED DESCRIPTION OF THE INVENTION

The invention resides in a method for the determination of the amount of a chemical moiety containing terbium or europium by applying an electrical pulse into an electrode immersed in a solution containing the moiety as a solute and/or adsorbed onto the surface of the electrode, and measuring the delayed light emission after some time from the end of the pulse. The measured light emission is taken as an indication of the amount of the chemical moiety present in the proximity of the electrode. The phenomenon to be measured will be called here delayed electroluminescence or DEL for brevity.

The chemical moiety has the structure $$(M-Z-Q)_n-L_m-Y_p$$

wherein M is terbium or europium, n is an integer greater or equal to one, m and p integers greater or equal to zero, provided that when Y is equal to one, m is equal to n, Z is a polydentate ligand, Q is a spacer arm, L is a linking group and Y is a substance to be described later.

In the simplest case m and p are both zero and n is one. In this case M-Z is a chelate of terbium or europium. One preferred structure of Z complexed to a lanthanide ion is without detailed description of the metal-ligand bonding:

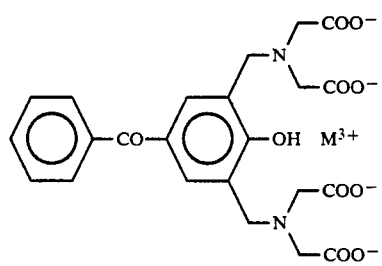

$M^{3+} = Tb^{3+}$ or $Eu^{3+}$

In this case the method can be used e.g. for the highly sensitive determination of terbium ion in solution as will be described in Example I. This invention is very useful in the binding assays such as immunoassay or nuclei acid hybridization techniques which are based on the dissociation of lathanide ion from the lanthanide-containing label and the subsequent DEL determination of lathanide ion in solution.

In a more complicated case $n,m \geq 1$ and $p \geq 1$, substance Y is then said to be labelled by a DEL label. Suitable substances Y include many biological substances, e.g. whole cells, subcellular particles, viruses, nucleic acids, nucleotides, oligonucleotides, polynucleotides, polysaccharides, proteins, polypeptides, enzymes, cellular metabolites, hormones, pharmacological agents, alkaloids, steroids, vitamins, amino acids, carbohydrates, serum-derived or monoclonal antibodies. Also synthetic substances, such as drugs, synthetic nucleic acids and synthetic polypeptides are within the scope of this invention. Substance Y is linked through linking groups L and spacer arms Q to chelates M-Z. The linking groups are those bivalent radicals generally used for labelling analyte molecules by probe molecules well known to those of ordinary skill in the art. The choice of the linking group is based on the substance Y to be labelled and the synthetic feasibility. The linking groups for DEL are the same as generally used for e.g. labelling substances by fluorescent labels for binding assays. These bivalent linking groups include a ureido, thioureido; an amide, such as —CONH—, —CONMe—; thioether, such as —S—, —S—S—; sulfonamide, such as —SO$_2$NH— and —SO$_2$NMe—. Polydentate ligand Z may be an aromatic compound having at least one chelating sidegroup such as —CH$_2$N(CH$_2$COOH)$_2$,

—CH$_2$—NCH$_2$CH$_2$N(CH$_2$COOH)$_2$,
    |
    CH$_2$COOH

—CH$_2$NCH$_2$CH$_2$N—CH$_2$CH$_2$N(CH$_2$COOH)$_2$, or
   |      |
   |    CH$_2$COOH
   CH$_2$COOH hydroxyl —OH or its corresponding anion, that is after removal of one or more protons. The purposes of the chelating sidegroups is to form a stable and kinetically inert complex with the lanthanide ions. Lanthanides are known for the lability of most of their complexes and the tendency to form strong coordinating bonds with oxygen donors. Consequently, a multidentate ligand with a large number of oxygen donors such as carboxylate groups is needed in order to achieve the stability and inertness required of a compound used for labelling purposes. One further reason for a multidentate ligand is that in order to increase the luminescence decay time of the lanthanide complex, as many water molecules as possible should be expelled from the coordination sphere of the lanthanide ion. It is well known that the luminescence decay time of terbium and europium complexes is inversely proportional to the number of OH bonds in the inner coordination sphere. The present method is based on the time resolution of luminescence and consequently a long decay time is analytically advantageous. Aminopolycarboxylic acids are known for their strong chelating tendencies with most polyvalent cations. An example is ethylenediaminetetraacetic acid (EDTA) which forms complexes with Tb(III) and Eu(III) with the stability constants of $10^{17.9}$ and $10^{17.4}$, respectively. Even more stable complexes are formed by diethylenetrlaminepentaacetic acid (DTPA), i.e. $10^{22.7}$ and $10^{22.4}$ for Tb(III) and Eu(III), respectively. The stability of these EDTA and DTPA complexes would be sufficient for labelling purposes, but these complexes lack two important properties to be useful as DEL labels. First of all, in order to exploit a compound as a label in any method, the compound should possess a binding arm which allows covalent bonding with the substance to be labelled. Secondly, a special requirement for a DEL label is the presence of at least one aromatic ring in the molecule. This aromatic ring serves as an energy acceptor and donor in the DEL process. In this process a short electric pulse is applied between two electrodes in contact with the sample containing the electroluminescent complex. In the immediate vicinity of one of the electrodes the aromatic ring of the labelling ligand receives an electron either directly from the electrode or by mediation of some reactive radical formed electrolytically during the pulse. The reactive radical could be e.g. hydrogen atom or solvated electron. The resulting radical of the ligand reacts further by donating the electron to some highly reactive electron acceptor in solution, formed also during the electric pulse. Examples of these electron acceptors are hydroxyl radical HO., sulfate monoanion radical SO$_4^-$· and superoxide radical HOO·. These reactions are highly energetic and the reformed ligand emerges in the electronically excited singlet or triplet state. The subsequent steps are well known from the photoluminescence mechanism of lanthanide complexes. The electronic energy is transferred by the internal conversion to the triplet state if this is not initially formed in the process. If the triplet energy level of the ligand and the electronically excited energy levels of lanthanide atom are not too far from each other, energy is transferred from the ligand triplet state to the energy levels of the lanthanide atom, provided that the triplet level is not lower than the lanthanide energy level. A further requirement for efficient energy transfer is that the lanthanide atom and the aromatic part of the ligand are not too distant in the molecule. The final step is the radiative transfer to the ground states of the lanthanide atom.

Ligand Z may bind to the linking group via a spacer arm Q consisting of a molecular chain the purpose of which is to keep the ligand and substance Y at a suitable distance from each other. The length of the spacer arm depends on the application. If the substance Y is a very large molecule, it is preferable to use a long spacer arm to keep the chelate part of the label molecule outside the labelled molecule Y in order to allow the efficient charge transfer required for DEL. Preferred spacer arms include $-C_6H_4-CO-$, $-C_6H_4-CH_2-$, $-CH_6H_4-CH_2CH_2-$ and $-(CH_2)_r-$, where $-C_6H_4-$ stands for 1,2-, 1,3- or 1,4-phenylene and r is an integer from 1 to 6. One preferred structure of the ligand is:

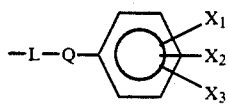

where the substituents of the benzene ring $X_1$, $X_2$ and $X_3$ are the said chelating sidegroups or hydrogen and at least one of them is the said chelating sidegroup. An example which illustrates the meaning of the linking group L, spacer arm Q and ligand Z is shown below:

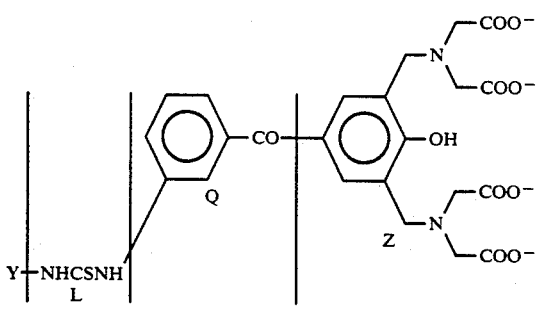

The method of this invention is useful to determine labelled moieties of interest, to employ labelled moieties to determine analytes of interest, or to use labelled analogues of analytes of interest.

The invention is useful to determine analytes of interest in both competitive and noncompetitive binding assays. These binding assays may be heterogeneous or homogeneous. Analogous binding assays are used also in nucleic acid hybridization techniques, where the DEL labels also find use, such as dot-blot and sandwich hydridization assays as well as hybridization assays employing affinity based collection and PCR (polymerase chain reaction) technology.

For instance, in a competitive immunoassay antibody is coated onto the electrode surface and antigen and antigen with a DEL label compete for the active sites of the antibody. The antigen now corresponds to substance Y and is one of the substances listed hereinabove. The amount of antibody-antigen complex on the electrode surface is quantitated by DEL either directly after immunoreaction or after a washing step and addition of suitable electrolyte solution containing e.g. peroxydisulfate. Alternatively homogeneous noncompetitive immunoassay can be achieved by immobilizing a "catching" antibody on the electrode surface. The sample antigens caught by those antibodies are quantitated with the use of DEL labelled antibodies that bind to a second site on the antigen. In this case antigens are the substances listed hereinabove in connection with the definition of Y.

A. Apparatus

No patent claims about the apparatus are made but a detailed description of it is given in order to give a clearer picture on the method of measurement.

The measuring system is composed of a pulse generator, potentiostat, a sample cell with two or three electrodes, an optional light filter or monochromator, a light detector and a gated integrator or photon counter. The pulse generator may be any generator which is capable of producing freely programmable pulse chains with adjustable amplitude.

The potentiostat may be a conventional three-electrodepotentiostat, or, if only two electrodes are used, a simple booster amplifier capable of delivering a few tens of milliamperes of current.

The sample cell and light detector are enclosed in the same light-tight chamber. The cell has two or three electrodes immersed into the electrolyte solution. In case of three electrodes one electrode is a reference electrode, one is an auxiliary electrode and one is a working electrode. These are connected to the potentiostat by the conventional way. Light emission is measured from the working electrode, which is made of any conducting material. Preferable material is oxide-covered metal, e.g. aluminum, tantalum, zirconium or hafnium. The reference electrode may be any conventional reference electrode, e.g. calomel electrode or Ag-AgCl electrode. The auxiliary electrode may be made of any conductive material, most often platinum. If only two electrodes are used the electrodes can be both made of the same material, e.g. aluminum, in which case light can be made to emit from both electrodes or the other electrode is made of different material. Alternatively the sample cup itself may be made of aluminum and it functions in this case as the working electrode from which light is emitted.

The light intensity from the working electrode is measured using a photomultiplier or a photodiode with an optional filter or monochromator in between, and the electrical signal from the light detector is brought to a gated integrator or a gated photon counter. Gating is synchronized with the pulses from the pulse generator with an appropriate delay.

B. Method

The sample to be measured for its DEL is a compound which is dissolved in solution or adsorbed onto the surface of the working electrode. The compound should have a slow decay of its electroluminescence. Preferential compounds are luminescent lanthanide complexes, preferably such as chelates of $Tb^{3+}$ or $Eu^{3+}$, which have their decay at the millisecond timescale. The compound may be measured itself or it may be bound as a label to the material to be assayed. In addition to the compound to be measured the electrolyte solution in the sample cell contains some electrolyte, preferably sulfate or acetate to increase the conductivity. An oxidizing compound such as peroxydisulfate, hydrogen peroxide or dissolved oxygen may be present in the solution. The function of the oxidizing agent is to produce highly reactive radicals by a direct or mediated electrolytic reduction, e.g. $S_2O_8^{-2}+e^-\rightarrow SO_4^{2-}+SO_4^{\cdot-}$ These radicals react with the luminescent compound producing light emission. Consequently electroluminescence is observed after a cathodic pulse to the working electrode. Potentially anodic pulses may be used for certain types of lanthanide compounds.

A sequence of cathodic pulses with a suitable duration and duty cycle depending on the luminescent compound is applied to the working electrode. The resulting light emission is measured after the end of the cathodic pulses using an appropriate gate width and delay. For the preferred terbium complexes the length of the cathodic pulse may vary from 0.2 ms to 5 ms, the delay after the pulse is 0.1 to 0.5 ms and the gate width from 2 ms to 10 ms. For the europium complexes the times are ca. 4 times shorter, that is 0.025–0.125 ms. The signal integrated during the open gate time is averaged for as many periods as is necessary to achieve the required signal-to-noise ratio.

The invention is further illustrated by references to the drawings of which:

EXAMPLE I

Standard curve for terbium by electroluminescence

Figure 1:
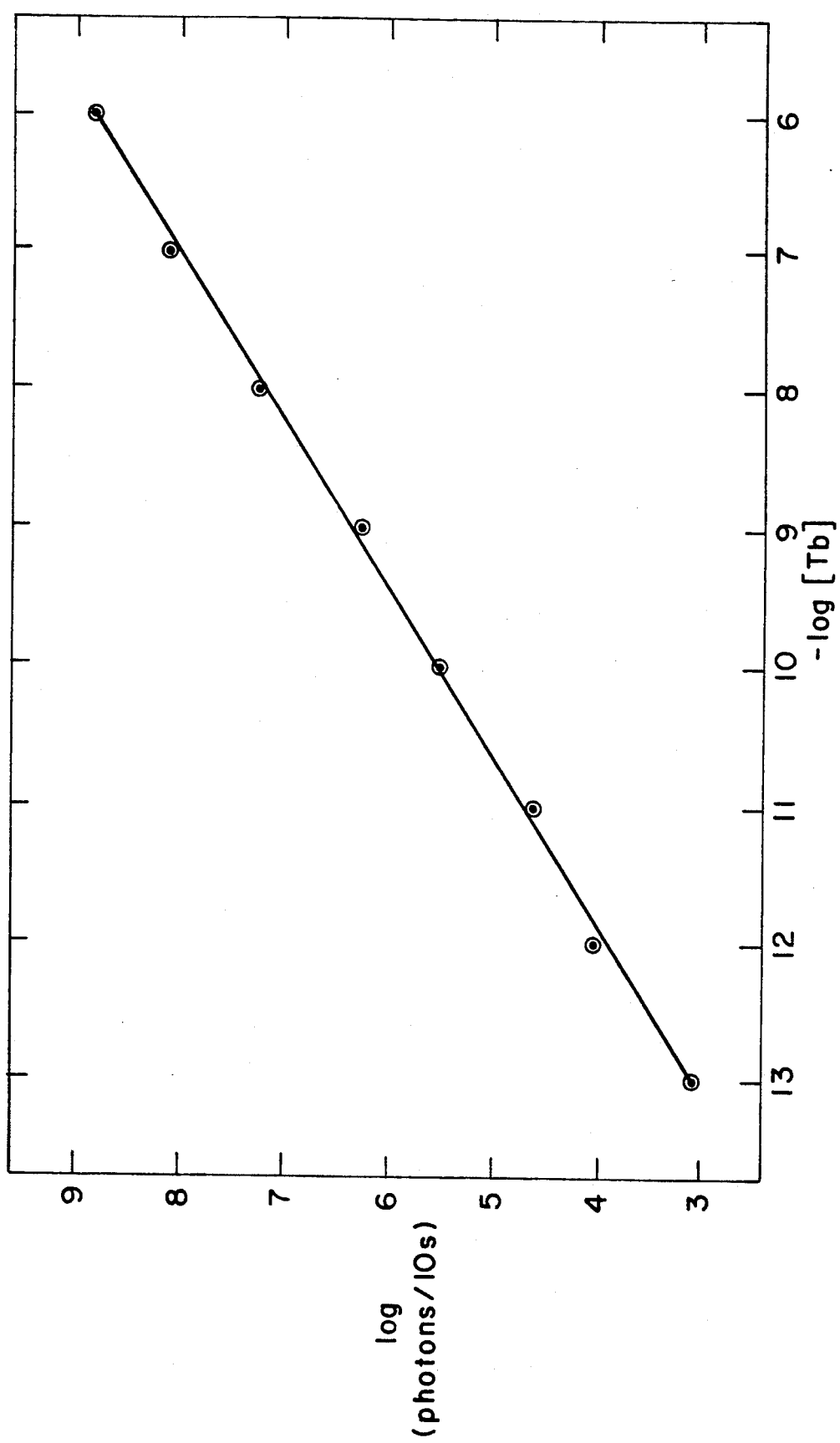
FIG. 1 shows the increase of log (photons/10 s against the increase of the log [Tb]

The sample solution in the example is 0.3M in sodium sulfate, 0.001M in potassium peroxydisulfate and $10^{-5}$M in 3,6-bis[N,N-bis(carboxymethyl)aminomethyl]-4-benzoylphenol, and adjusted to pH 11.2 with $5\times10^{-4}$M TRIS and NaOH. The DEL measurements were done in disposable cups made of aluminum sheet of 0.3 mm thickness and 99.9% purity. The other electrode was a short platinum wire. Increasing portions of terbium chloride were added and the delayed electroluminescence was measured by using cathodic pulses of 1 ms duration, 8.5 V amplitude and 4% duty cycle. The light emitted from the aluminum cup was detected by a photomultiplier and a two-channel photon counter (Stanford Research, Model SR400). The gate of one channel was open from 0.2 to 10 ms from the end of the cathodic pulse and the other channel counted the "dark current" photons from 10.2 to 20 ms. After 100 s counting time the contents of the two counter registers were subtracted from each other. Table 1 and FIG. 1 show the results.

TABLE I

| Terbium mol/L | Photons/100 s |
|---|---|
| $10^{-13}$ | 1,200 |
| $10^{-12}$ | 11,000 |
| $10^{-11}$ | 40,800 |
| $10^{-10}$ | 316,000 |
| $10^{-9}$ | 1,750,000 |
| $10^{-8}$ | 15,824,000 |
| $10^{-7}$ | 112,000,000 |

TABLE I-continued

| Terbium mol/L | Photons/100 s |
|---|---|
| $10^{-6}$ | 565,000,000 |

EXAMPLE II

Preparation of a labelling compound

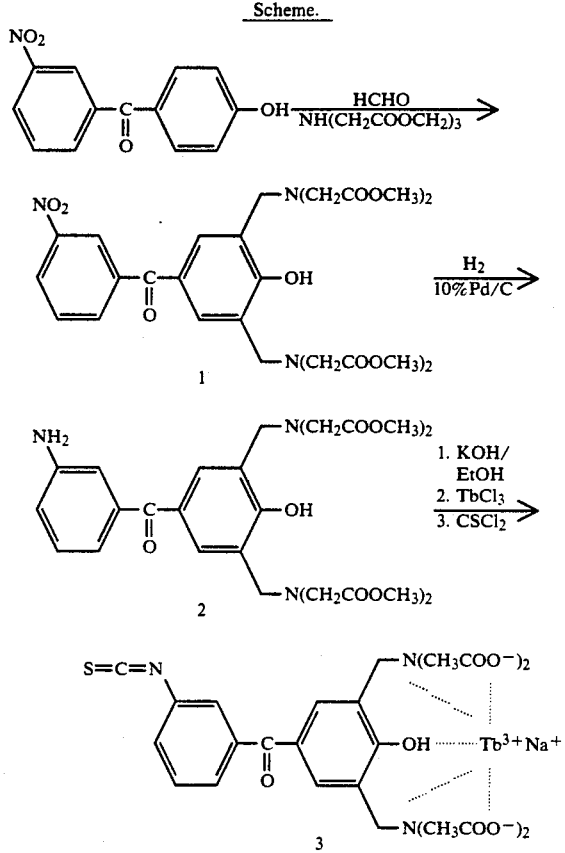

Synthesis of
4-(3-nitrobenzoyl)-2,6-bis[N,N-bis(methoxycarbonylmethyl)aminomethyl]phenol (1), To a solution of 37% aqueous formaldehyde (0.81 g, 10 mmol) in methanol (20 mL) was added dimethyl iminodiacetate (1.61 g, 10 mmol). The solution was concentrated in vacuo. Another portion of methanol (25 mL) was added to the residue and the solution was concentrated in vacuo. To the remainder 4-hydroxy-3'-nitrobenzophenone (1.22 g, 5 mmol) was added, and the mixture was heated with stirring at 110° C. for 20 h. The product was purified by chromatography on silica gel using chloroform as the eluent. The yield of yellowish oil was 1.76 g (60%). $^1$H NMR (CDCl$_3$): δ 3.48 (1H, s), 3.58 (8H, s), 3.71 (12H, s), 4.08 (4H, s), 7.73 (2H, s), 7.56–8.58 (4H, m).

Synthesis of
4-(3-aminobenzoyl)-2,6-bis[N,N-bis(methoxycarbonylmethyl)aminomethyl]phenol (2)

Compound 1 (0.89 g, 1.5 mmol) was stirred for 1 h in methanol (50 mL) with 10% Pd/C (90 mg) under hydrogen pressure of 50 psi. The mixture was filtered and evaporated in vacuo. The product was purified by chromatography on silica gel using light petroleum (b.p. 50°–70° C.)/ethyl acetate (2:5) as the eluent. The yield of yellowish oil was 0.40 g (48%). $^1$H NMR (CDCl$_3$): k 3.56 (1H, s), 3.59 (8H, s), 3.71 (12H, s), 4.01 (6H, broad s), 7.05–7.14 (4H, m), 7.70 (2H, s).

Synthesis of terbium complex of 4-(3-isothiocyanatobenzoyl)-2,6-bis[N,N-bis(carboxymethyl)aminomethyl]phenol (3)

Compound 2 (0.40 g, 0.71 mmol) was stirred for 3 h in 0.5M KOH-ethanol (20 mL) and water (5 mL). The mixture was neutralized with 1M HCl and evaporated in vacuo. Water (15 mL) and terbium chloride (0.27 g, 0.72 mmol) were added, pH was adjusted to 8.0 and the mixture was filtered. A few milliliters of acetone was added to the filtrate, and the terbium complex was filtered off. A small portion of the complex (68 mg) in water (3 mL) was added dropwise into a mixture of thiophosgene (31 μL, 0.4 mmol) and NaHCO$_3$ (42 mg, 0.5 mmol) in CHCl$_3$. After stirring for 1 h the water layer was separated and washed with CHCl$_3$. After adding a few milliliters of acetone the precipitate was filtered off and purified by chromatography on silica gel using CH$_3$CN/H$_2$O (4:1) as the eluent. The yield was 15 mg (38%; based on 2).

EXAMPLE III

Heterogeneous sandwich immunoassay of human pancreatic phospholipase A2

Labelling of sheep-anti-human PLA$_2$ antiserum 4-(3-Isothiocyanatobenzoyl)-2,6-bis[N,N-bis(carboxymethyl)aminomethyl]phenol terbium complex (3, Example II) was allowed to react with a 60-fold molar excess with the antibody at pH 9.5 for overnight. The labelled antibody was separated from excess free terbium complex on a column filled with Sephadex G-50 (1×5.5 cm) and Sepharose 6 B (1×5.2 cm) by using 0.1M sodium carbonate buffer pH 9.3, containing 9 g/L of NaCl and 0.05% NaN$_3$ as the eluting agent.

Coating of the aluminum cups

The aluminum cups (made of 99.9% aluminum foil of 0.3 mm thickness) were coated with anti-human PLA$_2$ antiserum by physical adsorption in 0.05M Tris-HCl buffer, pH 7.5, containing 9 g/L of NaCl and 0.05% NaN$_3$ (TSA-buffer) for overnight at room temperature. After coating the cups were washed with a wash solution (NaCl 9 g/L, NaN$_3$ 0.01% and Tween 20 0.2 g/L) and saturated with 0.1% bovine serum albumin (BSA for overnight and stored wet at +4° C.

Immunoassay

Figure 2:
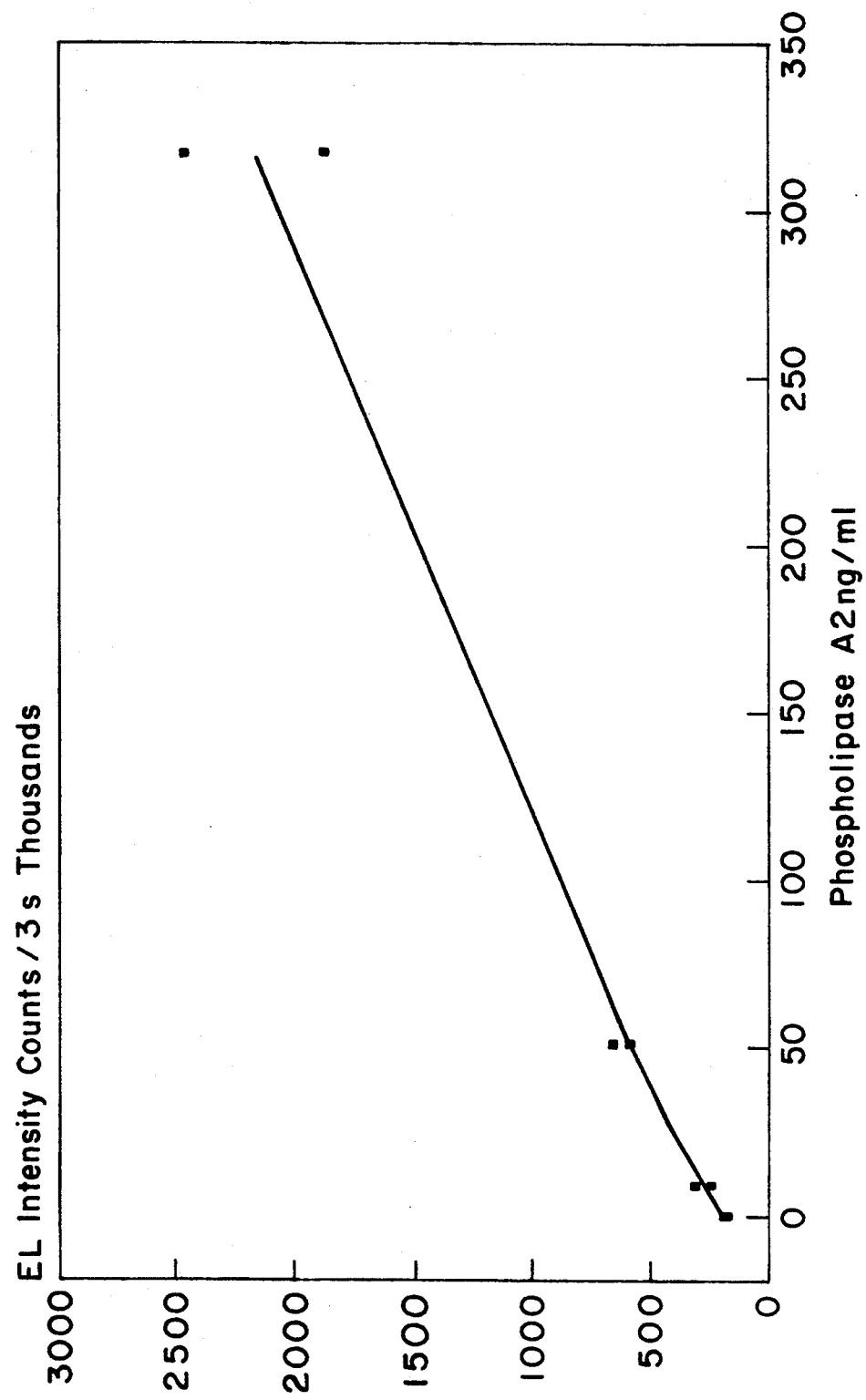
FIG. 2 shows the EL intensity counts/3 S thousands against the heterogeneous phospholipase A2 ng/ml in the sandwich immunoassay.

The aluminum cups were washed once with 500 μL of wash solution. Then 25 μL of standards containing 0, 9, 54 and 324 ng/mL of phospholipase A$_2$ in TSA-buffer (0.1% BSA) were added to the cups followed by 175 μL of Tb-labelled anti-PLA$_2$ antibody (570 ng/mL) in 0.05M Tris-H$_2$SO$_4$ buffer, pH 7.8, containing BSA 5 g/L, NaN$_3$ 0.5 g/L. After incubation for 3 h by continuously shaking the cups were washed 6 times with the wash solution. The electroluminescence was measured in the cups after adding 450 μL of 0.001M Tris-H$_2$SO$_4$ buffer, pH 8.7, containing 0.3 mol/L Na$_2$SO$_4$ and 0.001 mol/L K$_2$S$_2$O$_8$, as in Example I except that the counting time was only 3 s. The results of the assay is shown in Table 2 and FIG. 2.

TABLE 2

| PLA$_2$ ng/mL | Photons/10$^5$/3s | |
|---|---|---|
| 0 | 1.9 | 1.7 |
| 9 | 3.0 | 2.4 |
| 54 | 6.5 | 5.9 |
| 324 | 18.6 | 24.4 |

EXAMPLE IV

Homogeneous sandwich immunoassay of human pancreatic PLA$_2$ in serum

Coating of the cups and labelling of sheep-anti-human PLA$_2$ antiserum were done as in Example III.

Immunoassay

Figure 3:
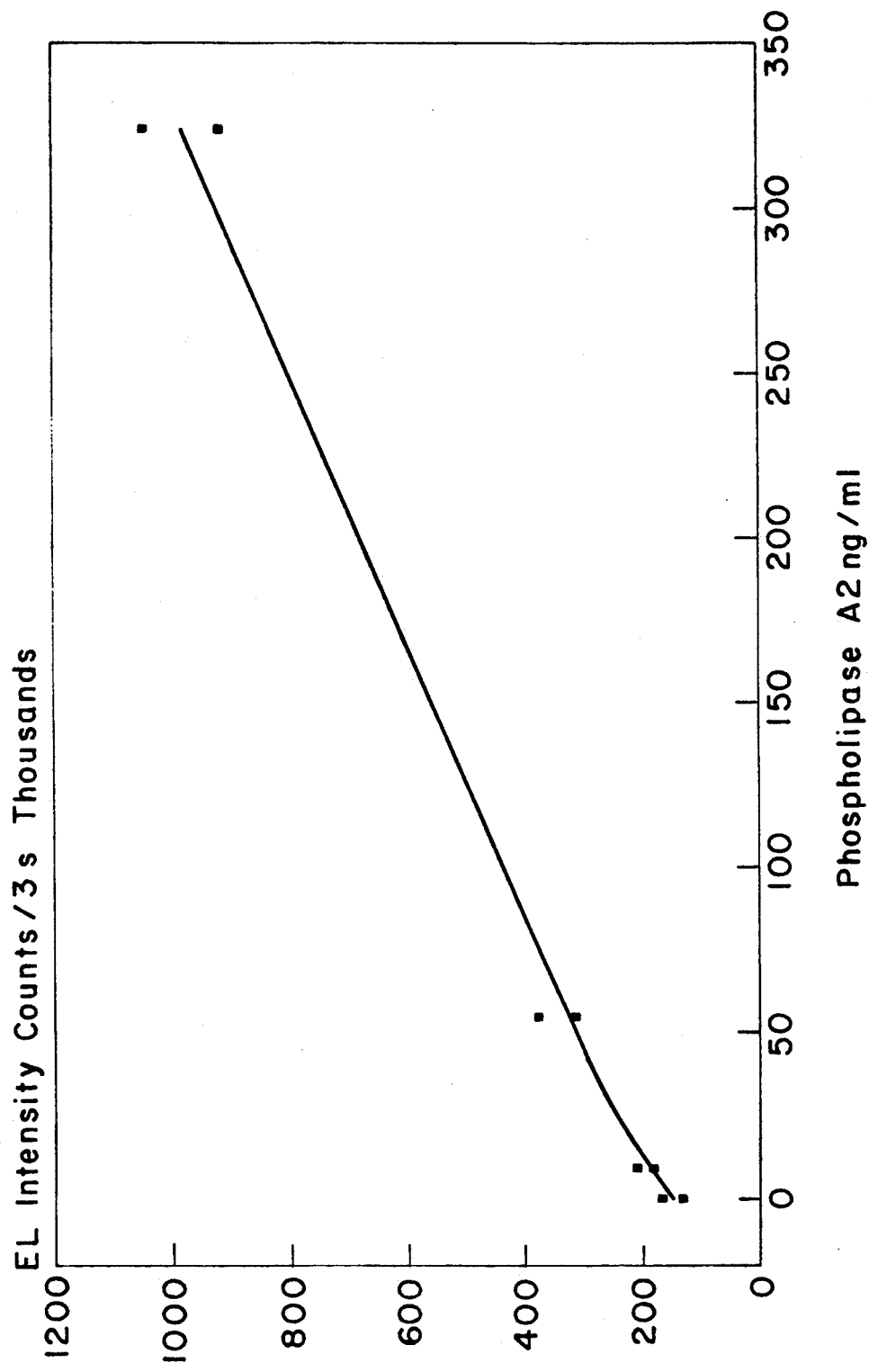
FIG. 3 shows the EL intensity counts/3 S thousands against the phopholipase A2 ng/ml in the homogeneous sandwich immunoassay.

The aluminum cups were washed once with 500 μL of wash solution. Then 25 μL of standards containing 0, 9, 54 and 324 ng/mL of phospholipase A$_2$ in human serum were added to the cups followed by 425 μL of Tb-labelled anti-PLA$_2$ antibody (235 ng/mL) in 0.05M Tris-H$_2$SO$_4$ buffer, pH 8.7, containing BSA 5 g/L, NaN$_3$ 0.5 g/L, 0.3 mol/L Na$_2$SO$_4$, 0.001 mol/L K$_2$S$_2$O$_8$. After incubation for 3 h by continuously shaking the electroluminescence was measured directly in the cups as in Example I except that the counting time was only 3 s. The results of the assay is shown in Table 3 and FIG. 3.

TABLE 3

| PLA$_2$ ng/mL | Photons/10$^5$/3s | |
|---|---|---|
| 0 | 1.6 | 1.5 |
| 9 | 1.8 | 2.1 |
| 54 | 3.1 | 3.7 |
| 324 | 9.1 | 10.4 |

We claim:
1. A method of determining the amount of a chemical moiety containing terbium, said chemical moiety being in an aqueous solution, said chemical moiety having the formula Tb-Z-wherein:

Z has the formula:

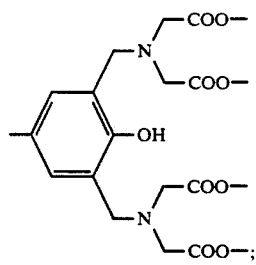

consisting essentially of the steps of:
(a) contacting a sample containing said chemical moiety with two electrodes one of which is made of aluminum;
(b) applying an electrical pulse across said electrodes;
(c) measuring the emitted light originating from one of the said electrodes starting after a delay of 0.1 to 0.5 ms from the end of the said electrical pulse and extending the measurement up to ten milliseconds;
(d) measuring the amount of said chemical moiety on the basis of the light intensity emitted in step (c).

2. A method of determining the amount of the antigen human pancreatic phospholipase $A_2$ in a sample which contains a chemical moiety containing terbium, consisting essentially of the steps of:
(a) contacting a sample containing said chemical moiety with two electrodes one of which is made of aluminum;
(b) applying an electrical pulse across said electrodes;
(c) measuring light originating from one of the said electrodes starting after a delay of 0.1 to 0.5 ms from the end of the said electrical pulse and extending the measurement up to ten milliseconds;
(d) measuring the amount of said chemical moiety on the basis of the light intensity emitted in step (c), said chemical moiety having the formula:

$Y_p\text{-}L_m\text{-}(Q\text{-}Z\text{-}Tb)_n$ wherein:
Z has the formula:

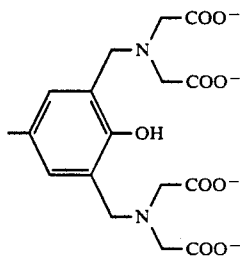

Y is an antibody of human pancreatic phospholipase $A_2$;
L is a bivalent linking group selected from the group consisting of ureido, thioureido, amide, substituted amide, thioether, sulfonamide, and a N-substituted sulfonamide;
Q is a spacer arm consisting of a molecular chain which separates the group Z and said antibody of human pancreatic phospholipase $A_2$ and is selected from the group consisting of $-C_6H_4-CO$, $-C_6H_4-CH_2-$, $-C_6H_4-CH_2CH_2-$ and $-(CH_2)_r$, wherein $-C_6H_4-$ stands for 1,2-, 1,3- or 1,4-phenylene and r is an integer from 1 to 6; said antibody of human phospholipase A2 being attached to Z through one or more linking groups L and spacer arm Q;
n is an integer equal to or greater than 1;
p is an integer greater than zero;
m is an integer equal to or greater than p.

3. The method according to claim 2, which is a homogeneous immunoassay and consists of the steps of:
(a) immobilizing an antibody specific to said human pancreatic phospholipase $A_2$ onto the surface of an aluminum electrode;
(b) forming a sample comprising said antigen and said chemical moiety;
(c) contacting the sample from step (b) between said electrode and another electrode;
(d) incubating said sample to form a reaction product on the surface of said aluminum electrode;
(e) applying an electrical pulse across the said electrodes;
(f) measuring light originating from one of the said electrodes starting after a delay of 0.1 to 0.5 ms from the end of the said electrical pulse and extending the measurement up to 10 milliseconds;
(g) using the light intensity emitted in step (f) as an indication of the amount of said chemical moiety and determining the amount of said antigen on the basis of the amount of said chemical moiety.

4. The method according to claim 2, wherein the method is a heterogeneous immunoassay and further comprises the step of separating the bound chemical moiety and the unbound chemical moiety prior to the application of electrical pulses across the electrodes and measurement of the emitted light.

* * * * *